United States Patent
Fishman

(10) Patent No.: US 8,296,163 B2
(45) Date of Patent: Oct. 23, 2012

(54) METHOD AND SYSTEM FOR MEDICAL TREATMENT REVIEW

(76) Inventor: Marc L. Fishman, Plantation, FL (US)

( * ) Notice: Subject to any disclaimer, the term of this patent is extended or adjusted under 35 U.S.C. 154(b) by 416 days.

(21) Appl. No.: 12/539,434

(22) Filed: Aug. 11, 2009

(65) Prior Publication Data

US 2011/0313786 A1    Dec. 22, 2011

(51) Int. Cl.
*G06Q 10/00* (2012.01)
*G06Q 50/00* (2012.01)

(52) U.S. Cl. ................. 705/2; 705/3; 600/300

(58) Field of Classification Search ............... 705/2–4; 600/300
See application file for complete search history.

(56) References Cited

U.S. PATENT DOCUMENTS

| | | |
|---|---|---|
| H958 H | 8/1991 | DeVita, Jr. et al. |
| 7,054,823 B1 | 5/2006 | Briegs et al. |
| 7,379,885 B1 | 5/2008 | Zakim |
| 2002/0072933 A1 | 6/2002 | Vonk et al. |
| 2002/0107705 A1 | 8/2002 | Boucher |
| 2002/0138306 A1 | 9/2002 | Sabovich |
| 2003/0105650 A1 * | 6/2003 | Lombardo et al. ........... 705/2 |
| 2003/0144885 A1 * | 7/2003 | Sachdev ................. 705/3 |
| 2003/0195770 A1 | 10/2003 | Fukushima |
| 2004/0044546 A1 | 3/2004 | Moore |
| 2004/0078220 A1 | 4/2004 | Jackson |
| 2004/0143460 A1 | 7/2004 | Marhaver |
| 2004/0249675 A1 | 12/2004 | Stark et al. |
| 2005/0197545 A1 | 9/2005 | Hoggle |
| 2005/0251415 A1 * | 11/2005 | Pak ................... 705/2 |
| 2005/0283384 A1 | 12/2005 | Hunkeler et al. |
| 2005/0283385 A1 | 12/2005 | Hunkeler et al. |
| 2006/0031100 A1 | 2/2006 | Huber |
| 2006/0116904 A1 | 6/2006 | Brem |
| 2008/0052118 A1 | 2/2008 | Iliff |
| 2008/0052129 A1 * | 2/2008 | Beraja et al. .............. 705/3 |
| 2008/0091472 A1 | 4/2008 | Hoppe |
| 2008/0114613 A1 | 5/2008 | VanKirk-Smith et al. |
| 2008/0281639 A1 | 11/2008 | Quinn et al. |
| 2009/0043612 A1 * | 2/2009 | Szela et al. ............. 705/3 |
| 2009/0063190 A1 | 3/2009 | Firozvi |
| 2009/0063192 A1 | 3/2009 | Giles |
| 2009/0125334 A1 | 5/2009 | Krishnan et al. |
| 2010/0145722 A1 * | 6/2010 | Zalta .................. 705/2 |

* cited by examiner

*Primary Examiner* — Luke Gilligan
(74) *Attorney, Agent, or Firm* — Novak Druce + Quigg

(57) ABSTRACT

A method of medical treatment review. The method can include the steps of receiving patient data into a patient database in which the patient data at least includes a diagnosis of the patient and providing one or more treatment protocols for the patient for selection by a treating provider in which the treatment protocols are pre-approved for the patient diagnosis. The method can also include the steps of analyzing a selection of a treatment protocol by the treating provider and generating an authorization of the selected treatment protocol based on predefined criteria. Generating the authorization of the selected treatment protocol can include generating the authorization without any peer review if the selected protocol meets the predefined criteria or generating the authorization following peer review if the selected protocol does not meet the predefined criteria.

15 Claims, 2 Drawing Sheets

US 8,296,163 B2

METHOD AND SYSTEM FOR MEDICAL TREATMENT REVIEW

FIELD OF THE INVENTION

The subject matter herein relates to the field of medical treatments and more particularly, to the field of approval for such medical treatments.

BACKGROUND OF THE INVENTION

Healthcare costs have exploded over the past several decades, and health insurers and government agencies have implemented procedures to minimize such expenses. For example, insurance companies typically review procedures performed on patients by physicians and will normally only pay for costs associated with approved treatments. Even so, this process has not limited the increasing costs associated with healthcare in this country. Moreover, current fee structures are skewed to favor more expensive treatment drugs. In particular, doctors are typically provided with a small percentage of the cost of a treatment used on a patient, and this arrangement causes treating physicians to choose more expensive pharmaceuticals, as opposed to lower cost drugs that are just as effective. As such, there is a need for a system and method that improves oversight of medical treatment.

SUMMARY OF THE INVENTION

A method of medical treatment review is described herein. The method can include the steps of receiving patient data into a patient database in which the patient data at least includes a diagnosis of the patient and providing one or more treatment protocols for the patient for selection by a treating provider. The treatment protocols can be pre-approved for the patient diagnosis. The method can also include the steps of analyzing a selection of a treatment protocol by the treating provider and generating an authorization or a recommended authorization of the selected treatment protocol based on predefined criteria. As an example, generating an authorization of the selected treatment protocol can include generating the authorization without any peer review if the selected protocol meets the predefined criteria or generating the authorization following peer review if the selected protocol does not meet the predefined criteria.

The peer review can include establishing a relationship between the treating provider and a treatment reviewer to determine whether to generate an authorization for the selected treatment protocol. The treatment reviewer can be, for example, a specialist in the field associated with the diagnosis of the patient and the provided treatment protocols. Moreover, the peer review can further include seeking input from an authorized agent following the establishment of the relationship between the treating provider and the treatment reviewer. The method can also include the steps of informing the treating provider of a status of the authorization and informing a primary care agent of the selected treatment protocol and any details of a peer review if such a review was conducted.

In another arrangement, the method can include the step of determining whether to apply a normalization fee for the selected treatment protocol. As an example, the normalization fee can be applied to increase the amount of profit that the treating provider would realize for the selected treatment protocol. As another example, the normalization fee can be a flat rate fee to be paid to the treating provider per treatment session for the patient. The method may also include the step of adjusting the number of treatment protocols available for selection by the treating provider if an initial selected treatment protocol was unsuccessful in treating the patient. Adjusting the number of treatment protocols available for selection by the treating provider can include eliminating from selection the initial selected treatment protocol that was unsuccessful in treating the patient and any equivalent treatment protocols.

A system for medical treatment review is also described. The system can include a patient database that can receive patient data from a treating provider in which the patient data includes at least a diagnosis of a disease of a patient and can include a treatment protocol database that is coupled to the patient database. The treatment protocol database can be populated with one or more treatment protocols that can provide guidelines for treating patients with various diseases. The system can also have a protocol approval module that is configured to receive the patient data and a treatment protocol that is selected by the treatment provider. The protocol approval module can analyze the patient data and the selected treatment protocol and can generate an automatic approval or forward the selected treatment protocol and the patient data for a peer review process.

The system can also include a peer review workstation that is configured to receive the selected treatment protocol and the patient data, thereby enabling a treatment reviewer to determine whether the selected treatment protocol should be authorized or recommended for authorization. In addition, the protocol approval module can be further configured to selectively generate a normalization fee that can be designed to increase the profit realized by the treating provider for the selected treatment protocol, which can offset the loss of revenue that may occur when a less costly protocol is chosen. Further, the protocol approval module can be configured to selectively adjust the option of selecting certain treatment protocols from the treatment protocol database based on an initial unsuccessful treatment of the patient.

Another method of treatment review by a treatment reviewer is presented. This method can include the steps of receiving patient data and a selected treatment protocol for a patient from a treating provider in which the selected treatment protocol is part of an approved listing of treatment protocols and conducting a peer review of the patient data and the selected treatment protocol. The peer review can be conducted by a treatment reviewer, who can be a specialist in the field, to determine whether to approve the selected protocol in view of other unselected treatment protocols that are part of the approved listing of treatment protocols. Conducting the peer review at least includes performing an exchange of information between the treatment reviewer and the treating provider. The method can also include the step of providing results of the peer review to the treating provider.

In one arrangement, the peer review can be conducted only if the selected treatment protocol is not automatically approved based on certain predefined criteria. The method can also include the steps of informing a primary care agent of the selected treatment protocol and any details of the peer review and selectively conducting an appellate review of the peer review if the treating provider maintains the selection of the selected treatment protocol.

Yet another method of selecting a treatment protocol by a treating provider is presented here. This method can include the steps of entering patient data into a patient database and selecting a treatment protocol from a list of pre-approved treatment protocols in which a treatment protocol can be pre-approved based on the patient data. The method can also include the step of receiving an authorization for the selected treatment protocol in which the authorization or recommendation of authorization can be automatically generated or generated following a peer review that determines that other unselected treatment protocols are unsuitable for the patient.

The method can also include the step of receiving a normalization fee for the selected treatment protocol based on predefined criteria in which the normalization fee can be a flat rate that can be received for treatment sessions for the patient and can be higher than the amount of profit that the treating provider would receive based on a percentage fee of the selected treatment protocol. The normalization fee can be designed to eliminate the incentive to choose one protocol over another based on the profitability of the protocol. When a normalization fee is applied to less profitable protocols, the profitability of all protocols in the group can be similar.

In one embodiment, the patient can be an existing patient, and the number of treatment protocols that are available for selection is different than the number of treatment protocols that were available for selection at the initial entry of the patient data. This arrangement is based on the understanding that patients who fail to respond to a treatment protocol or who relapse after receiving a treatment protocol are unlikely to respond to similar protocols in the future. By eliminating from the group of available treatment protocols those protocols that are very likely to be ineffective, the system minimizes the probability that patients will be treated with ineffective protocols.

Additional aspects will be set forth in the description which follows, and in part will be obvious from the description, or may be learned by practice of the embodiment. The aspects will be realized and attained by means of the elements and combinations particularly pointed out in the appended claims. It is to be understood that both the foregoing general description and the following detailed description are exemplary and explanatory only and are not restrictive.

BRIEF DESCRIPTION OF THE DRAWINGS

Several embodiments are shown in the drawings. It is expressly noted, however, that the subject matter herein is not necessarily limited to the arrangements and instrumentalities shown in the drawings.

DETAILED DESCRIPTION

Figure 1:
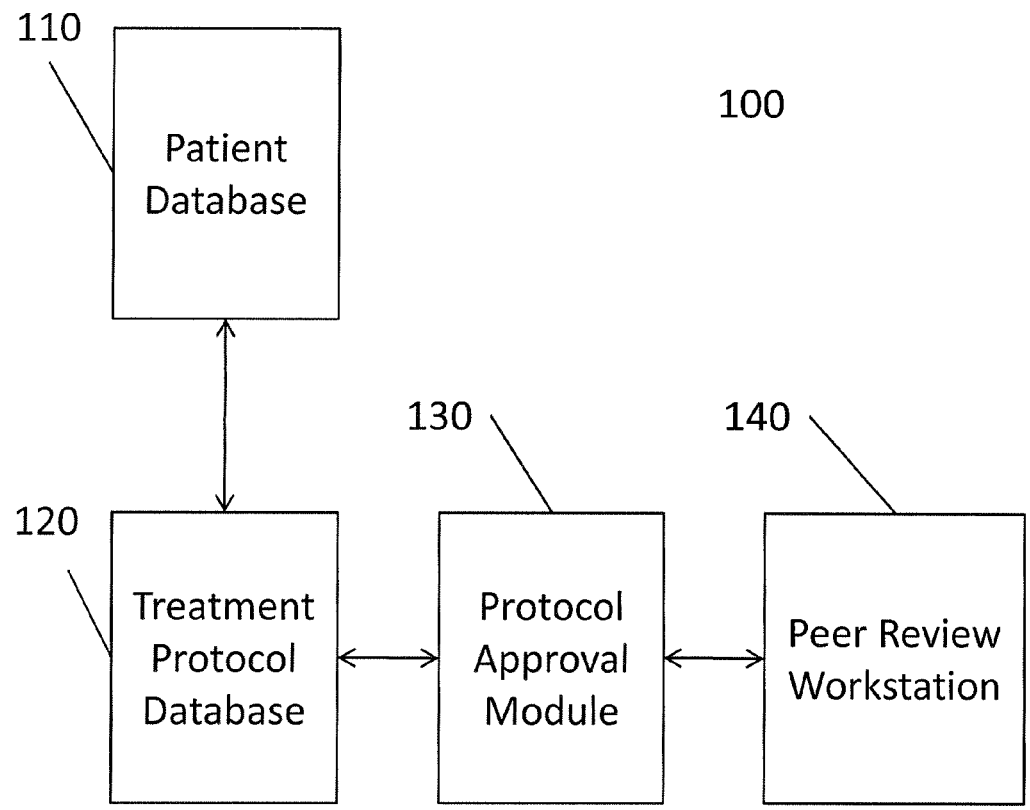
FIG. 1 is an illustration of an exemplary system for medical treatment review.

As noted earlier, healthcare costs in this country continue to skyrocket, and solutions are needed to get such expenses under control. As such, a method of medical treatment review that streamlines and maximizes efficiencies in patient treatments while simultaneously assuring that patients are treated according to nationally recognized guidelines is described below. The method can include the steps of receiving patient data into a patient database in which the patient data at least includes a diagnosis of the patient and providing one or more treatment protocols for the patient for selection by a treating provider in which the treatment protocols are pre-approved for the patient diagnosis. The method can also include the steps of analyzing a selection of a treatment protocol by the treating provider and generating an authorization of the selected treatment protocol based on predefined criteria. As an example, generating the authorization of the selected treatment protocol can include generating the authorization without any peer review if the selected protocol meets the predefined criteria or generating the authorization following peer review if the selected protocol does not meet the predefined criteria. This process provides a review of pre-approved treatments to ensure that the most economical and/or appropriate protocol is selected by the treating provider without affecting the efficacy of the strategy developed to treat the patient.

The terms "a" or "an," as used herein, are defined as one or more than one. The term "plurality," as used herein, is defined as two or more than two. The term "another," as used herein, is defined as at least a second or more. The terms "including" and/or "having," as used herein, are defined as comprising (i.e., open language). The term "coupled" as used herein is defined as connected, although not necessarily directly, and not necessarily mechanically. That is, "coupled" may also include two or more components that are wirelessly connected together.

The term "patient" is defined as any living thing that requires or may require medical attention and includes human beings and animals. The term "patient data" means any information that is associated with a patient and that is used to select a treatment for that patient. A "treatment protocol" means any plan for treating a particular disease or medical condition that has been pre-approved by an organization that is recognized by the medical community for providing guidelines or advice for such disease or condition. The term "diagnosis" means the identification of a disease or medical condition of a patient that may require treatment. The term "treating provider" means any person who provides medical treatment to a patient and may include persons not necessarily licensed to provide such treatment. A "patient database" is defined as any component or group of components configured to receive and store information that is associated with a patient. Moreover, a "treatment protocol database" means any component or group of components configured to store any number of treatment protocols that may be selected by a treatment provider. The terms "approve(d)" or "authorize(d)" are defined as express approvals or authorizations by a first party for a course of action or merely a recommendation for a second party to approve or authorize a course of action.

Referring to FIG. 1, an example of a system 100 for medical treatment review is shown. In one arrangement, the system 100 can include a patient database 110, a treatment protocol database 120 that can be coupled to the patient database 110 and a protocol approval module 130. Although the protocol approval module 130 is shown as being a separate component in FIG. 1, the subject matter described herein is not so limited, as the module 130 may be part of the treatment protocol database 120 or even the patient database 110. The system 100 may also include a peer review workstation 140, which may also be coupled to the protocol approval module 130. Each of these components may be linked together through any suitable network, including wired or wireless connections.

As an example, the patient database 110 can store any suitable type of information that is associated with a patient being treated by a treating provider. This information may be entered into the patient database 110 by the treating provider or any other authorized individual. Examples of such information include the patient's sex, height and weight, blood type, age, allergies or any diagnoses and other medical conditions and the extent of any diagnosis or medical condition. The treating provider may be, for example, a physician, a veterinarian, a nurse, or a paramedic or any other individual capable of providing some form of medical care. In some circumstances, the patient and the treating provider may be the same individual. To comply with privacy concerns, the patient database 110 may be a secure database in which only a treating provider who is authorized by the patient may access the patient's information contained in the patient database 110. This treating provider may have access to information in the patient database 110 that is associated with all the patients for whom the provider is responsible. Additionally, multiple treating providers may be able to enter patient data associated with their patients into the patient database 110 and later access such information.

In one arrangement, the treatment protocol database 120 may contain one or more treatment protocols for various diseases and medical conditions. These treatment protocols can typically include guidelines and advice for treating such ailments and can be designed by, for example, organizations that are recognized by the medical community. As an example, one or more of the treatment protocols may be plans for treating a patient with cancer that are in accordance with the guidelines of the National Comprehensive Cancer Network or some other suitable organization. As will be explained in more detail below, these treatment protocols may be pre-approved for treatment of a particular disease or medical condition. The treating provider may then select at least one of the treatment protocols from the list of pre-approved treatment protocols contained in the treatment protocol database 120. It is understood that the number of pre-approved treatment protocols may be adjusted based on, for example, new discoveries or scientific studies.

The protocol approval module 130 may receive the patient data and the selected treatment protocol and may be configured to perform an analysis of this information. To perform such an analysis, the approval module 130 may include any suitable combination of software and hardware, including processors and/or logic circuitry. Following the analysis, the protocol approval module 130 may automatically approve or authorize the selected treatment protocol and can inform the treatment provider and other authorized individuals of such approval or authorization. In another arrangement, the protocol approval module 130, following the analysis, may forward the selected treatment protocol and the patient data to the peer review workstation 140 for a peer review process.

The peer review workstation 140 may include any suitable type of hardware and software components to enable a treatment reviewer to perform a peer review process, such as conducting a review of the patient data and selected treatment protocol. The treatment reviewer can also have access to all the treatment protocols that are part of the treatment protocol database 130. The peer review workstation 140 may also include any suitable means of communications to enable the treatment reviewer to communicate with various authorized parties regarding the peer review process.

Figure 2:
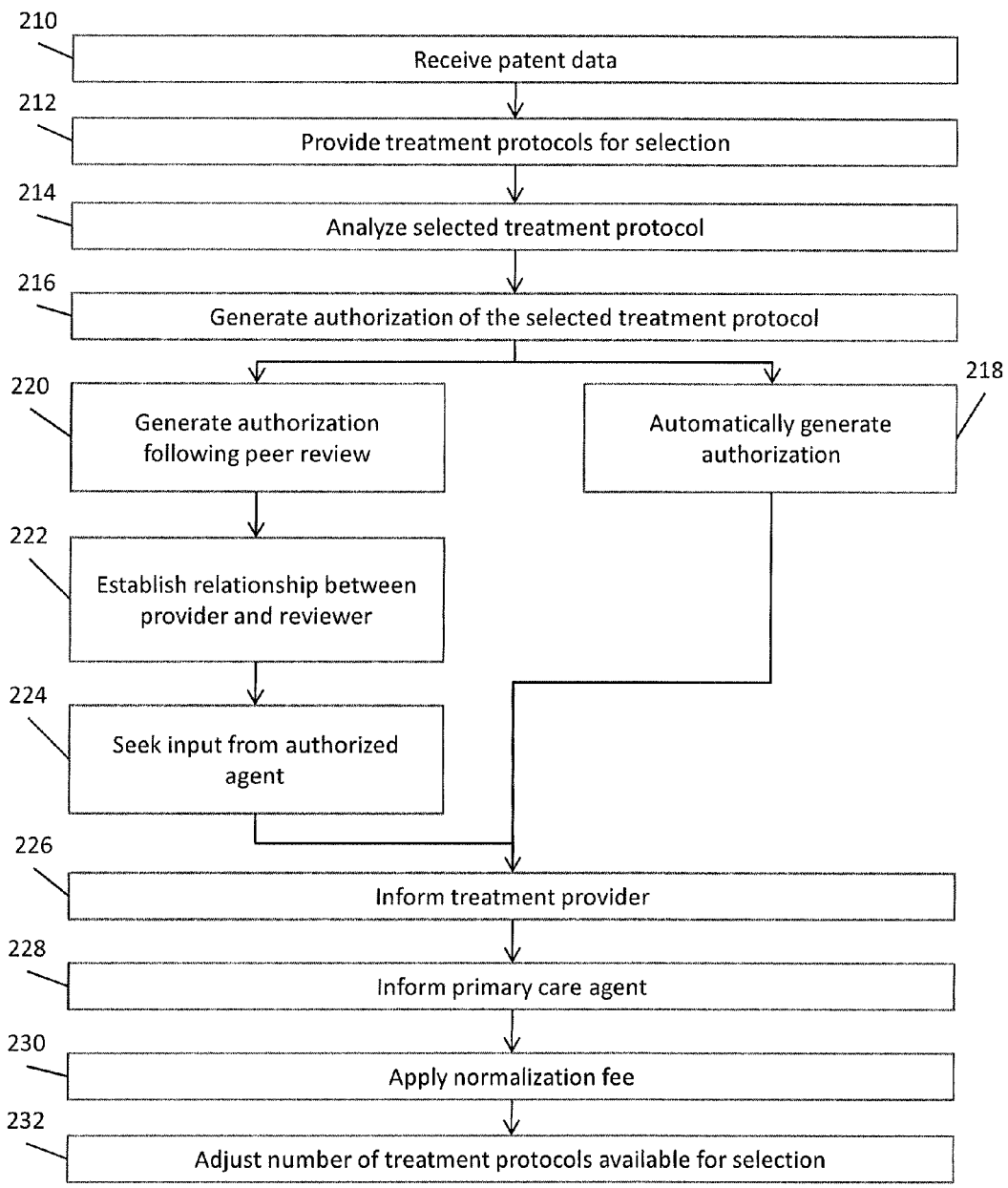
FIG. 2 is an illustration of an exemplary method for medical treatment review.

Referring to FIG. 2, an example of a method 200 of treatment review is illustrated. When describing this method, reference may be made to FIG. 1, although it is understood that the method 200 may be practiced in other suitable systems. It must be noted that the described method 200 is not necessarily limited to these particular steps, as the method 200 may contain a greater or fewer number of steps in comparison to what is pictured. Moreover, the method 200 is not limited to the particular order illustrated here.

At step 210, patient data can be received into the patient database 110 in which the patient data at least includes a diagnosis of the patient. At step 212, one or more treatment protocols for the patient can be provided for selection by a treating provider in which the treatment protocols are pre-approved for the patient diagnosis. A specific example of a patient having stage 2 breast cancer will be presented here, although it is understood that the method 200 is in no way limited to this particular illustration.

The treating provider, as described earlier, can enter the patient's data in the patient database 110, and in this instance, the diagnosis is stage 2 breast cancer. The treatment protocol database 120 can receive this information and can cause one or more pre-approved treatment protocols to be displayed to the treatment provider. Here, multiple treatment protocols for treating this particular form of cancer and its progression can be displayed. The treatment protocols can be pre-approved treatment plans for each disease or medical condition for which they are designed. A "pre-approved treatment protocol" is a guideline or set of guidelines or strategy for treating a particular disease or medical condition that has been designated as an acceptable form of treatment for such disease or medical condition by an organization that is familiar with the disease or medical condition at issue. As an example, in this case, the treatment protocols can all be geared towards treating stage 2 breast cancer, and the protocols can be based on the guidelines of the National Comprehensive Cancer Network or some other suitable organization that specializes in cancer research.

Referring back to the method 200, a selection of a treatment protocol by a treating provider can be analyzed, as shown at step 214, and at step 216, an authorization of the selected treatment protocol based on predefined criteria can be generated. In one arrangement, generating the authorization can be automatically performed without any peer review if the selected treatment protocol meets the predefined criteria, as shown at step 218.

In an alternative arrangement, if the selected protocol does not meet the predefined criteria, then the authorization may be generated following peer review, as shown at step 220. In this alternative arrangement, a relationship can be established between the treating provider and a treatment reviewer to determine whether to generate the authorization, as shown at step 222. Moreover, at step 224, as part of the peer review, input can be sought from one or more authorized agents following the establishment of the relationship between the treating provider and the treatment reviewer. In either arrangement, at step 226, the treating provider can be informed of a status of the authorization, and a primary care agent can be informed of the selected treatment protocol and any details of a peer review if such a review was conducted, as shown at step 228. Examples of these processes will now be provided.

Once the treating provider selects a pre-approved treatment protocol, the protocol approval module 130 can analyze the selection in view of certain predefined criteria. The predefined criteria can be any suitable number of factors that can indicate the effectiveness of a treatment protocol, such as toxicity, ability to improve a patient's condition and overall cost. For example, the treating provider may select a treatment protocol that includes the use of one or more drugs for treating breast cancer that are within acceptable cost ranges but that are just as effective as other, more expensive treatments. In addition, the selected protocol may be appropriate for use by the particular patient in question, as determined by the protocol approval module 130. Such a selection can be automatically approved or authorized by the protocol approval module 130, and the module 130 may signal the treating provider, through any suitable means, of the status of the authorization.

On the other hand, however, the treating provider may select a treatment protocol that, while pre-approved for treatment of breast cancer, is far more expensive than other available treatment protocols but that does not present an increase in utility or effectiveness. Further, the selected treatment protocol may be more toxic for the particular patient in question when compared to other treatment protocols. In these situations, the protocol approval module 130 may flag the selected treatment protocol and designate it for peer review, forwarding the relevant information to the peer review workstation 140.

As another example, the treating provider may select a treatment protocol that—while pre-approved for treatment of breast cancer—may be less effective than other treatment protocols. This exemplary selected treatment protocol, however, may also have fewer adverse effects, thus limiting its utility to special circumstances. Special circumstances may include, but are not limited to, pre-existing medical conditions, patient age, and previous treatments. In these situations, the protocol approval module 130 may flag the selected treatment protocol and designate it for peer review, irrespective of the cost of the protocol, forwarding the relevant information to the peer review workstation 140.

The treatment reviewer can then analyze the selected treatment protocol and the patient data to determine whether to approve or authorize the selected protocol. The term "treatment reviewer" is defined as any entity, including a human being or a machine, capable of conducting a review of patient data and selected treatment protocols to determine whether a treatment protocol that is more appropriate than the selected treatment protocol based on various factors, such as cost or efficacy, is available for the patient. As an example, the treatment reviewer can be a specialist in the field associated with the diagnosis of the patient and the provided treatment protocols. In the example described thus far, the treatment reviewer may be an experienced oncologist. In addition, the phrase "peer review" or "peer review process" is defined as any procedure to be conducted by a treatment reviewer to determine whether a more appropriate treatment protocol is available.

As part of the review, the treatment reviewer may contact the treating provider to discuss or otherwise acquire more information from the treating provider. Alternatively, the protocol approval module 130 may generate a signal that causes a notice to be sent to the treating provider asking the treating provider to contact the treatment reviewer. This notice can include any suitable amount of information to enable the treating provider to contact the treatment reviewer and may or may not give an indication as to why the selected treatment protocol has been designated for peer review.

Once the relationship is established, the treating provider may provide an explanation as to why the selected treatment protocol is the proper protocol to employ for the patient. The treatment reviewer may also explain why an unselected treatment protocol is more appropriate for use, based on, for example, its lower cost or increased effectiveness. This exchange of information can occur through any suitable means, whether electronic (for example, phone, e-mail, on-line meeting) or in-person meetings.

As an example, the treatment reviewer may suggest a protocol treatment that relies on less expensive drugs that would be just as effective in treating the patient, and the treating provider may agree with the suggestion and select the suggested protocol, thereby lowering the amount of money needed for the patient's healthcare. The treatment reviewer or some other suitable entity can then approve or authorize the new selected treatment protocol and can inform the treating provider of the status of the authorization.

Conversely, the treating provider may explain to the treatment reviewer that the treatment protocol suggested by the treatment reviewer, although a pre-approved protocol, includes a regimen that is not suitable for treating the patient. For example, some of the drugs of the suggested treatment protocol may be toxic to the patient, or the treating provider may have evidence, based on the patient's health history, that demonstrates that the suggested treatment protocol will not be as effective in treating the patient. The treatment reviewer may agree with the explanation provided by the treating provider and may approve the originally selected treatment protocol, even if it is more expensive than some of the other pre-approved but unselected treatment protocols. The treating provider can then be informed of the status of the authorization.

In one arrangement, if the treatment reviewer does not accept the treating provider's rationale, the treatment reviewer may seek input from one or more authorized agents, similar to an appellate process. The term "authorized agent" is defined as any entity, including a human being or a machine, other than the treatment reviewer capable of conducting a review of patient data and selected treatment protocols to determine whether the protocol treatment selected by the treating provider and the justification provided by the treating provider for such selection warrants approval or authorization over the objections raised by the treatment reviewer. For example, in the case where the patient has breast cancer, the authorized agent may be another oncologist who has several years of experience in dealing with treatment of patients afflicted with the cancer. This appellate process may include the treatment reviewer receiving input from a team of authorized agents, if so desired.

If the authorized agent agrees with the treatment reviewer, the treatment reviewer may maintain the objection and may not authorize or may not recommend the authorization of the selected treatment protocol. If the authorized agent, however, disagrees with the treatment reviewer, the treatment reviewer may remove the objection and authorize the selected treatment protocol. In either case, the treating provider can be informed of the status of the authorization.

In addition to providing notice to the treating provider concerning the status of the authorization of the selected protocol, such information may also be provided to other interested parties. For example, a primary care agent responsible for managing the healthcare of the patient may receive a notice of the selected treatment protocol and any details of a peer review if such a review was conducted. This notice may include the authorization or the declination of such authorization by the treatment reviewer. The primary care agent can be, for example, a primary care physician employed by a health insurance company or a government agency who is responsible for approving payment of healthcare costs of the patient by the health insurance company or government agency. After receiving this information, the primary care agent may make an informed decision as to whether to authorize payment for the selected treatment protocol.

As previously noted, current fee structures that are in place in the healthcare industry may cause physicians to favor more expensive drugs over those that are cheaper yet that are just as effective. For example, continuing with the breast cancer example, assume that two of the most effective treatments for stage 2 of this cancer are Treatment A and Treatment B. Therapeutically, these chemotherapeutic protocols are equivalent. Treatment A, however, costs about $890 for treatment, while Treatment B is about $27,700 for treatment. The profit for a treating physician for use of Treatment A is about $44.50 over eight months; however, for Treatment B, the physician will realize about $1,385 in profit for the same time period. Clearly, there is an incentive for the treating doctor to choose the more expensive treatment, even though such treatment is no more effective than the more moderately priced one.

Referring once again to the method 200 of FIG. 2, at step 230, it can be determined whether to apply a normalization fee for the selected treatment protocol, and this normalization fee can be applied to increase the amount of profit that the treating provider would realize for the selected treatment protocol. The term "normalization fee" means any adjustment of compensation to a treating provider that would increase the incentive for the treating provider to select a particular treatment protocol. As an example, the normalization fee can be a flat rate fee that can be paid to the treating provider per treatment session for the patient.

To demonstrate the use of a normalization fee, a discussion will be presented that makes use of the two treatments described above. For example, a normalization fee of approximately $150 per treatment session for the patient can be applied to the treatment protocol associated with Treatment A for stage 2 breast cancer. Assuming monthly treatments for six months, this would generate about $900 in profit for the treating provider. The treating provider would also receive a small percentage, such as five percent, of the overall cost of the treatment, which is consistent with standard practice. In this case, this amount would be five percent of $890, or $44.50. As a result, the total profit for the treating provider would be slightly under $950.

In comparison, the more expensive Treatment B would result in a total profit of $1,385, and no normalization fee would be applied. Because the treating provider would receive a higher profit than would normally be realized for the much cheaper and equally therapeutic Treatment A, there would be less incentive for the treating provider to select the vastly more expensive Treatment B. In summary, the normalization fee can be designed to "level the playing field" so that the profit from less expensive protocols can be approximately equal to the profit from more expensive protocols. It is understood that the above description is merely exemplary in nature, and the subject matter described herein can be applied to various other treatment protocols and numerical values.

This normalization fee can be selectively applied to treatment protocols based on certain criteria, such as costs and effectiveness. In the example above, the normalization fee can be applied to Treatment A in view of its relatively limited expense but not to Treatment B based on its high cost. As another example, there may be a case where two pre-approved treatment protocols are roughly the same cost, but one may be considered less toxic or more effective in treating patients. If desired, a normalization fee may be applied to the more effective protocol treatment to increase the chances of its selection. Additionally, there may be some cases where no normalization fee will be applied to any pre-approved treatment protocols for a certain disease or medical condition. For instance, all the protocol treatments pre-approved for a certain cancer may be relatively expensive, with little or insignificant difference in their prices. Because the profit potential for each of these treatment protocols would be similar, it may not be necessary to attempt to adjust the incentive for the treating provider to select a particular treatment protocol.

Referring back to the method 200, at step 232, the number of treatment protocols available for selection by the treating provider may be adjusted if an initial selected protocol was unsuccessful in treating the patient. For example, considering the exemplary patient diagnosed with stage 2 breast cancer, assume the patient completed an initial treatment that was unsuccessful. By unsuccessful, the patient may not have shown any improvement in her condition or may have relapsed after the initial treatment. At this point, the treating provider may wish to begin another treatment protocol. When doing so, the number of treatment protocols available for selection in the treatment protocol database 120 may be adjusted. In one particular example, the initially selected treatment protocol and equivalent treatment protocols may be removed from the list of available treatment protocols, thereby reducing the number of available protocols, because these protocols have been shown to be ineffective. That is, the system 100 can automatically eliminate treatment protocols that may not be of value based on the patient's treatment history. This adjustment in the number of available protocols can be repeated if the patient continues to show no improvement or relapses again.

Embodiments herein can take the form of hardware and/or software elements. In one embodiment, the subject matter is implemented in software, which includes but is not limited to firmware, resident software, microcode, and the like. Furthermore, the subject matter can take the form of a computer program product accessible from a computer-usable or computer-readable medium providing program code for use by or in connection with a computer or any instruction execution system. The computer program product can include all the features enabling the implementation of the methods described herein, and which when loaded in a computer system is able to carry out these methods. Computer program in the present context means any expression, in any language, code or notation, of a set of instructions intended to cause a system having an information processing capability to perform a particular function either directly or after either or both of the following: a) conversion to another language, code or notation; b) reproduction in a different material form.

For the purposes of this description, a computer-usable or computer readable medium can be any apparatus that can contain, store, communicate, propagate, or transport the program for use by or in connection with the instruction execution system, apparatus, or device. The medium can be an electronic, magnetic, optical, electromagnetic, infrared, or semiconductor system (or apparatus or device) or a propagation medium. Examples of a computer-readable medium include a semiconductor or solid state memory, magnetic tape, a removable computer diskette, a random access memory (RAM), a read-only memory (ROM), a rigid magnetic disk and an optical disk. Current examples of optical disks include compact disk—read only memory (CD-ROM), compact disk—read/write (CD-R/W) and DVD.

A data processing system suitable for storing and/or executing program code can include at least one processor coupled directly or indirectly to memory elements through a system bus. The memory elements can include local memory employed during actual execution of the program code, bulk storage, and cache memories which provide temporary storage of at least some program code in order to reduce the number of times code must be retrieved from bulk storage during execution. Input/output or I/O devices (including but not limited to keyboards, displays, pointing devices, etc.) can be coupled to the system either directly or through intervening I/O controllers. Network adapters may also be coupled to the system to enable the data processing system to become coupled to other data processing systems or remote printers or storage devices through intervening private or public networks. Modems, cable modem and Ethernet cards are just a few of the currently available types of network adapters.

The foregoing description of embodiments has been presented for the purposes of illustration. The description is not intended to limit the invention to the precise forms disclosed. Indeed, modifications and variations will be readily apparent from the foregoing description. Accordingly, it is intended that the scope of the claims not be limited by the detailed description provided herein.

What is claimed is:

1. A computer-implemented method of medical treatment review, comprising:
   receiving patient data into a patient database, wherein the patient data at least includes a diagnosis of the patient;
   providing a plurality of treatment protocols for the patient for selection by a treating provider, wherein the treatment protocols are pre-approved for the patient diagnosis, and wherein each of the plurality of treatment protocols are associated with a cost and a effectiveness;
   receiving a selection of one of the plurality of treatment protocols by the treating provider to yield a selected treatment protocol;
   generating an authorization of the selected treatment protocol based on predefined criteria;
   and subsequent to the authorization and via a processor, determining whether at least one normalization fee for the selected treatment protocol should be applied based at least on a comparison of the cost and the effectiveness for the selected treatment protocol with respect to other ones of the plurality of treatment protocols; and
   applying the at least one normalization fee to increase an amount of profit the treatment provider would realize for the selected treatment protocol to exceed a customary amount of profit for the selected treatment protocol, wherein an amount for the at least one normalization fee is determined based at least on a difference in the cost and the effectiveness for the selected treatment protocol with respect to other ones of the plurality of treatment protocols.

2. The method of claim 1, wherein generating an authorization of the selected treatment protocol comprises:
   generating the authorization without any peer review if the selected protocol meets the predefined criteria, and
   generating the authorization following peer review if the selected protocol does not meet the predefined criteria.

3. The method of claim 2, wherein the peer review comprises presenting, at a peer review workstation, at least the patient data and the selected treatment protocol to a treatment reviewer, and receiving one of an authorization or an objection to the selected treatment protocol from the peer review workstation.

4. The method according to claim 3, wherein the peer review further comprises delivering at least the patient data and the selected treatment protocol to an authorized agent, other than the treating provider and the treatment reviewer, responsive to the receiving of the objection.

5. The method according to claim 4, further comprising the steps of:
   informing the treating provider of a status of the authorization; and
   informing a primary care agent of the selected treatment protocol and any details of a peer review if such a review was conducted.

6. The method according to claim 1, wherein the at least one normalization fee increases the amount of profit that the treating provider would realize for the selected treatment protocol to at least approach an amount of profit as for other ones of the treatment protocols pre-approved for the patient diagnosis for which the effectiveness is similar and the cost is higher as compared to the selected treatment protocol.

7. The method according to claim 1, wherein at least one normalization fee is a flat rate fee to be paid to the treating provider per treatment session for the patient.

8. The method according to claim 1, further comprising adjusting the number of treatment protocols available for selection by the treating provider if an initial selected treatment protocol was unsuccessful in treating the patient.

9. The method according to claim 8, wherein adjusting the number of treatment protocols available for selection by the treating provider comprises eliminating from selection at least the selected treatment protocol that was unsuccessful in treating the patient.

10. The method of claim 1, wherein at least one other normalization fee is applied for the selected treatment protocol when the authorization is generated without any peer review.

11. A system for medical treatment review, comprising:
    a processor;
    a patient database that receives patient data from a treating provider, wherein the patient data includes at least a diagnosis of a disease of a patient;
    a treatment protocol database that is populated with one or more treatment protocols that provide guidelines for treating patients with various diseases; and
    a computer readable medium having storing instructions for causing the processor to:
      receive the patient data from the patient database, a treatment protocol that is selected by the treating provider for the patient, and treatment protocol data from the treatment protocol database that is associated with the disease of the patient,
      analyze the patient data and the selected treatment protocol based at least on the treatment protocol data,
      based on the analysis, automatically generate an approval for the selected treatment protocol if predefined criteria are met, else forward the selected treatment protocol and the patient data for a peer review process to generate the approval,
      responsive to the approval, determining whether at least one normalization fee for the selected treatment protocol should be applied based at least on a comparison of the cost and the effectiveness for the selected treatment protocol with respect to other treatment protocols pre-approved for the patient diagnosis, and
      applying the at least one normalization fee to increase an amount of profit the treatment provider would realize for the selected treatment protocol to exceed a customary amount of profit for the selected treatment protocol, wherein an amount for the at least one normalization fee is determined based at least on a difference in the cost and the effectiveness for the selected treatment protocol with respect to other ones of the plurality of treatment protocols.

12. The system according to claim 11, further comprising a peer review workstation that is configured to receive the selected treatment protocol and the patient data, thereby enabling a treatment reviewer to determine whether the selected treatment protocol should be authorized.

13. The system according to claim 11, wherein the computer-readable medium further comprises instructions for causing the processor to compute the at least one normalization fee to increase the profit realized by the treating provider for the selected treatment protocol to at least approach an amount of profit as for other ones of the treatment protocols pre-approved for the patient diagnosis for which the effectiveness is similar and the cost is higher as compared to the selected treatment protocol.

14. The system according to claim 11, wherein the the computer-readable medium further comprises instructions for causing the processor to selectively adjust the option of selecting certain treatment protocols from the treatment protocol database based on an initial unsuccessful treatment of the patient.

15. The system of claim 11, wherein the computer-readable medium further comprises instructions for causing the processor to apply at least one other normalization fee for the selected treatment protocol when the authorization is generated without any peer review.

* * * * *